United States Patent
Simoneau et al.

(10) Patent No.: US 11,000,413 B2
(45) Date of Patent: May 11, 2021

(54) OPHTHALMIC LASER SURGICAL SYSTEM AND METHOD IMPLEMENTING SIMULTANEOUS LASER TREATMENT AND OCT MEASUREMENT

(71) Applicant: AMO Development, LLC, Santa Ana, CA (US)

(72) Inventors: Michael J. Simoneau, Morgan Hill, CA (US); David A. Dewey, Sunnyvale, CA (US); Javier G. Gonzalez, Palo Alto, CA (US)

(73) Assignee: AMO Development, LLC, Santa Ana, CA (US)

( * ) Notice: Subject to any disclaimer, the term of this patent is extended or adjusted under 35 U.S.C. 154(b) by 94 days.

(21) Appl. No.: 16/278,029

(22) Filed: Feb. 15, 2019

(65) Prior Publication Data
US 2020/0261267 A1    Aug. 20, 2020

(51) Int. Cl.
*A61F 9/008*    (2006.01)
*A61B 3/10*    (2006.01)

(52) U.S. Cl.
CPC ............ *A61F 9/0084* (2013.01); *A61B 3/102* (2013.01); *A61F 9/00814* (2013.01); *A61F 2009/0088* (2013.01); *A61F 2009/00851* (2013.01)

(58) Field of Classification Search
CPC .............. A61F 9/0084; A61F 9/00814; A61F 2009/00851; A61F 2009/0088; A61F 9/008–2009/00897; A61B 3/102
USPC ............................................. 606/4–6, 10–12
See application file for complete search history.

(56) References Cited

U.S. PATENT DOCUMENTS

| | | |
|---|---|---|
| 5,459,570 A | 10/1995 | Swanson et al. |
| 5,748,352 A | 5/1998 | Hattori |
| 5,748,898 A | 5/1998 | Ueda |
| 6,053,613 A | 4/2000 | Wei et al. |

(Continued)

FOREIGN PATENT DOCUMENTS

EP    2664309 B1    6/2016

OTHER PUBLICATIONS

International Search Report and Written Opinion for Application No. PCTIB2020050875, dated Apr. 13, 2020, 7 pages.

(Continued)

*Primary Examiner* — Jonathan T Kuo
(74) *Attorney, Agent, or Firm* — Johnson & Johnson Surgical Vision, Inc.

(57) ABSTRACT

In an ophthalmic laser surgical system, a real-time optical coherence tomography (OCT) measurement method acquires OCT data during laser treatment. The treatment laser beam and OCT sample beam are generated simultaneously, and the optical delivery system scans them simultaneously in the eye tissue, where the focus of the treatment laser beam and the focus of the OCT beam coincide with each other in space. While both beams simultaneously scanned in the eye tissue, the OCT device detects returned OCT light from the sample during a data acquisition period, and generates an OCT A-scan based on the detected OCT light. Based on the A-scan, a controller determines a structure of the eye in a depth direction relative to the focus of the OCT beam, and controls the operations ophthalmic laser surgical system accordingly. One exemplary application is the formation of an arcuate corneal incision in cataract surgery.

20 Claims, 6 Drawing Sheets

(56) References Cited

U.S. PATENT DOCUMENTS

| | | | |
|---|---|---|---|
| 6,111,645 | A | 8/2000 | Tearney et al. |
| 9,301,687 | B2 | 4/2016 | Kemp |
| 9,492,322 | B2 | 11/2016 | Goldshleger et al. |
| 9,504,609 | B2 | 11/2016 | Kurtz |
| 9,693,905 | B2 | 7/2017 | Palanker et al. |
| 9,820,887 | B2 * | 11/2017 | Goldshleger ....... A61F 9/00834 |
| 2009/0137993 | A1 * | 5/2009 | Kurtz .................. A61F 9/00736 606/6 |
| 2011/0202046 | A1 * | 8/2011 | Angeley ................ A61B 3/107 606/6 |
| 2012/0316545 | A1 | 12/2012 | Blumenkranz et al. |
| 2014/0128731 | A1 * | 5/2014 | Gonzalez ............... A61B 3/107 600/427 |
| 2015/0141972 | A1 | 5/2015 | Woodley et al. |
| 2016/0074221 | A1 | 3/2016 | Tassignon et al. |
| 2016/0367399 | A1 | 12/2016 | Goldshleger et al. |
| 2017/0140560 | A1 | 5/2017 | Kraus et al. |
| 2017/0209042 | A1 | 7/2017 | Matz et al. |
| 2017/0266048 | A1 | 9/2017 | Friedman et al. |
| 2017/0332899 | A1 * | 11/2017 | Walsh .................... A61B 3/154 |
| 2018/0028355 | A1 | 2/2018 | Raksi |
| 2018/0207031 | A1 | 7/2018 | Woodley et al. |
| 2018/0214309 | A1 | 8/2018 | Al-Qaisi et al. |

OTHER PUBLICATIONS

Kaufmann Daniel et al. "Selective retina therapy enhanced with optical coherence tomography for dosimetry control and monitoring: a proof of concept study." Biomedical optics express, 2018, vol. 9(7), pp. 3320-3334.

\* cited by examiner

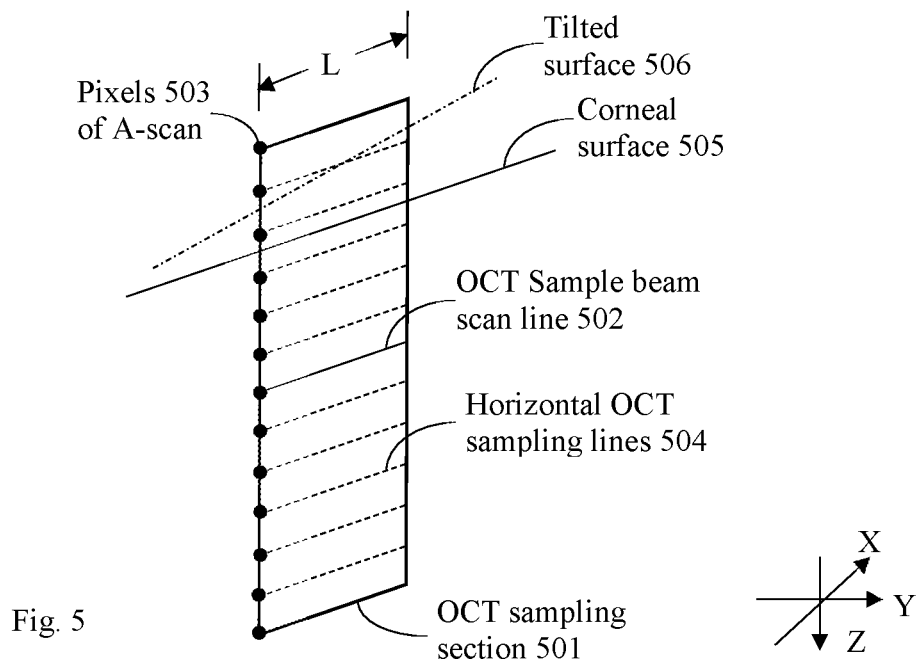

Fig. 5

S701: Simultaneously generating a treatment laser beam using an ultrafast laser source and generating an OCT beam using an OCT device S702: Simultaneously delivering a focus of the treatment laser beam and a focus of the OCT beam to a sample using an optical delivery system, the focuses of the treatment laser beam and OCT beam coinciding with each other in space, including simultaneously scanning the focuses of the treatment laser beam and OCT beam in a horizontal direction according to a treatment scan pattern S703: While the OCT beam is scanned in the sample, the OCT device detecting returned OCT light from the sample over a data acquisition period, and generating an A-scan using the detected light S704: Based on the A-scan, a controller determining the sample structure in the depth direction relative to the focus of the OCT beam S705: Based on the determination, the controller controlling operations of the ultrafast laser source, OCT device and optical delivery system

Fig. 7

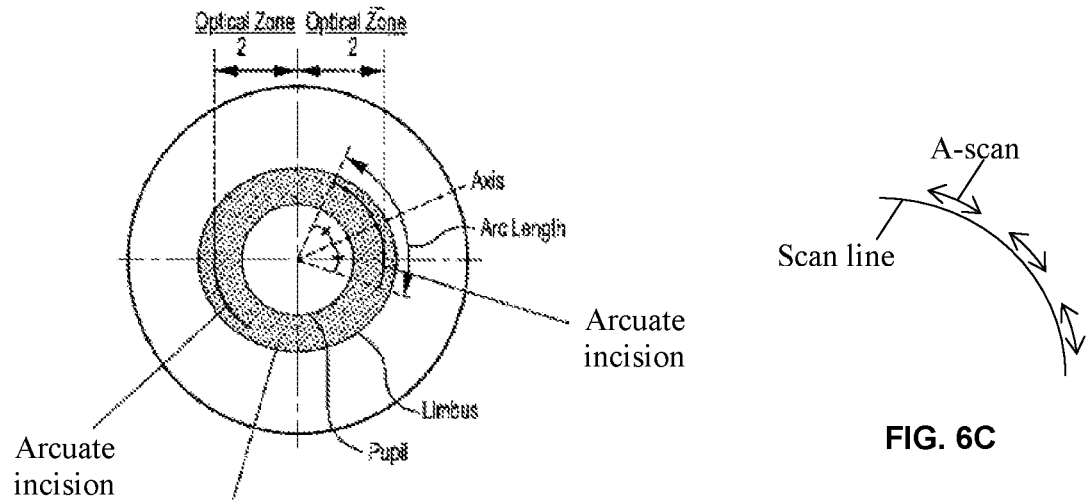
FIG. 6A
FIG. 6C
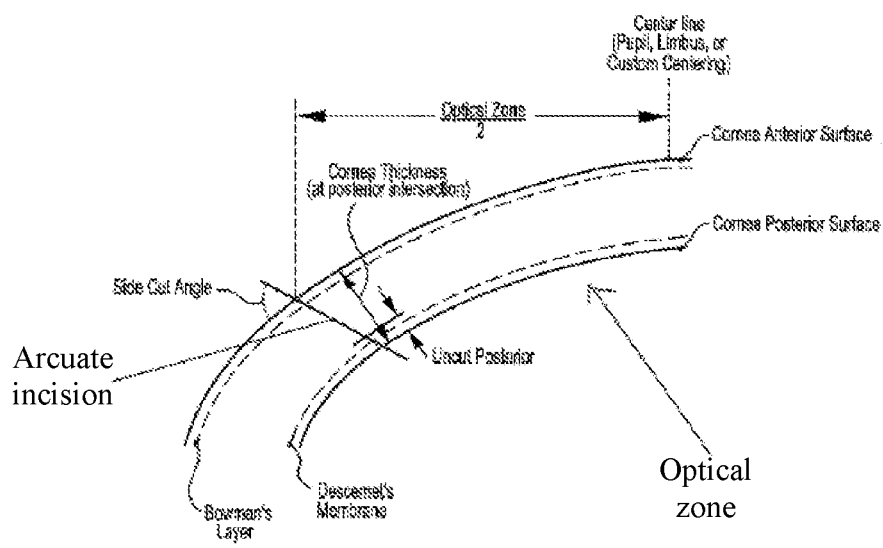
FIG. 6B

OPHTHALMIC LASER SURGICAL SYSTEM AND METHOD IMPLEMENTING SIMULTANEOUS LASER TREATMENT AND OCT MEASUREMENT

BACKGROUND OF THE INVENTION

Field of the Invention

The present invention relates to ophthalmic laser surgical procedures and systems, and in particular, it relates to such procedures and systems utilizing an optical coherence tomography (OCT) system for real-time monitoring of the laser treatment locations.

Description of Related Art

Ophthalmic laser surgery systems are well known and can be used to make incisions in and/or to otherwise photodisrupt various ocular tissues, including the cornea, the lens capsule, the crystalline lens, etc. For example, in a laser cataract procedure, a laser beam is used to form a small incision in the cornea to provide access to interior of the eye, to form an opening in the anterior lens capsule (anterior capsulotomy or capsulorhexis), and to soften and fragment the cataract lens nucleus. The fragmented lens nucleus is then extracted using a surgical tool inserted via the small incision on the cornea, and a synthetic foldable intraocular lens (IOL) is inserted through the same incision into the eye and implanted in the lens capsule.

A cataract surgery may include three types of cornea incisions: arcuate incisions, primary incisions ("primary cataract incisions", or "cataract incisions") and sideport incisions. Primary incisions and sideport incisions are generally multiplanar structures that create openings to allow the physician access into the anterior chamber, for example, to insert an aspiration tool and other instruments, to insert the IOL, etc. Arcuate incisions may be used to correct a patient's astigmatism. For instance, they may adjust the curvature of the cornea to a more spherical shape by relaxing stresses along the meridian on which they are placed.

Precise delivery of the laser focus spot for treatment is paramount in laser eye surgery. This is particular important, for example, during formation of the arcuate incisions in cataract surgery. The laser system settings for forming arcuate incisions in the cornea, both anterior penetrating and intrastromal, requires a minimum uncut distance in the posterior side of the cornea of approximately 100 µm. This distance is small in comparison to the vertical tolerance of laser delivery system, which is approximately 75 µm. In addition, patient movement can erode the margin of error. Therefore, accurate calibration of the depth of laser beam focus is important.

In some current technologies, depth calibration is performed using a bubble surface test. The tests is performed by placing a plastic object with a nearly horizontal flat surface in front of the objective lens of the laser system at a known distance, and immersing the surface in water. The treatment laser beam is then scanned in multiple planes parallel to the plastic surface, where the planes are located at decreasing depths by small decrements. When the laser focus reaches out of the plastic and into the water, it produces visible cavitation bubbles in water. Thus, the formation of bubble indicates that the laser is located at the plastic surface. By adjusting the treatment depth relative to that indicated by the bubble appearance, the laser cutting depth can be calibrated. Another calibration procedure, which may be performed daily before treating patients, is similar to the bubble formation method above, but uses a water-immersed plastic hemisphere.

SUMMARY

The calibration procedures described above, however, do not address the problem of treatment location variability induced by patient movement, because the calibration is not performed in real time.

The present invention is directed to a real-time OCT imaging technique that can generate OCT measurement data simultaneously with the delivery of treatment laser focus to the eye.

An object of the present invention is to provide a real-time imaging method that can address the problem of variation of treatment location resulting from patient movement.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic laser surgical process, which includes: a laser device and an optical coherence tomography (OCT) device simultaneously generating a treatment laser beam and an OCT light beam, respectively; an optical delivery system simultaneously delivering a focus of the treatment laser beam and a focus of the OCT light beam to a sample, the sample including a patient's eye, wherein the focus of the treatment laser beam and the focus of the OCT light beam coincide with each other in space; the OCT device detecting returned OCT light from the sample during a data acquisition period while the focus of the treatment laser beam and the focus of the OCT light beam are simultaneously delivered to the sample, and generating an OCT A-scan based on the detected OCT light, the A-scan being a one-dimensional array of intensity values in a depth direction representing structural properties of the sample; and a controller analyzing the A-scan to determine a structure of the sample in a depth direction relative to the focus of the OCT light beam, and based on the determination, controlling operations of the laser source, the OCT device and the optical delivery system. Preferably, the OCT device is a frequency domain OCT device.

In another aspect, the present invention provides an ophthalmic surgical laser system, which includes: a laser device configured to generate a treatment laser beam; an optical coherence tomography (OCT) device configured to generate an OCT light beam, and to detect a returned OCT light from a sample during a data acquisition period to generate an OCT A-scan based on the detected OCT light, the A-scan being a one-dimensional array of intensity values in a depth direction representing structural properties of the sample; an optical delivery system configured to deliver a focus of the treatment laser beam and a focus of the OCT light beam to the sample, the sample including a patient's eye; and a controller coupled to the laser device, the OCT device and the optical delivery system, configured to: control the laser device and the OCT device to simultaneously generate the treatment laser beam and the OCT light beam, respectively; control the optical delivery system to simultaneously deliver the focus of the treatment laser beam and the focus of the OCT light beam to the sample, wherein the focus of the treatment laser beam and the focus of the OCT light beam coincide with each other in space; receive the A-scan generated by OCT device during the data acquisition period while the focus of the treatment laser beam and the focus of the OCT light beam are simultaneously delivered to the sample, and analyze the A-scan to determine a structure of the sample in a depth direction relative to the focus of the OCT light beam; and based on the determination, control operations of the laser source, the OCT device and the optical delivery system.

In another aspect, the present invention provides a computer program product comprising a computer usable non-transitory medium (e.g. memory or storage device) having a computer readable program code embedded therein for controlling a data processing apparatus, the computer readable program code configured to cause the data processing apparatus to execute the above process.

It is to be understood that both the foregoing general description and the following detailed description are exemplary and explanatory and are intended to provide further explanation of the invention as claimed.

BRIEF DESCRIPTION OF THE DRAWINGS

FIG. 5 schematically illustrates an OCT sampling section scanned by the OCT sample beam during an A-scan according to an embodiment of the present invention.

FIGS. 6A and 6B illustrate an arcuate incision in a cornea.

FIG. 6C schematically illustrates generating multiple A-scans along a continuous scan line of the treatment pattern.

FIG. 7 is a flow chart showing a laser ophthalmic treatment procedure employing real-time OCT monitoring according to an embodiment of the present invention.

DETAILED DESCRIPTION OF PREFERRED EMBODIMENTS

Figure 1:
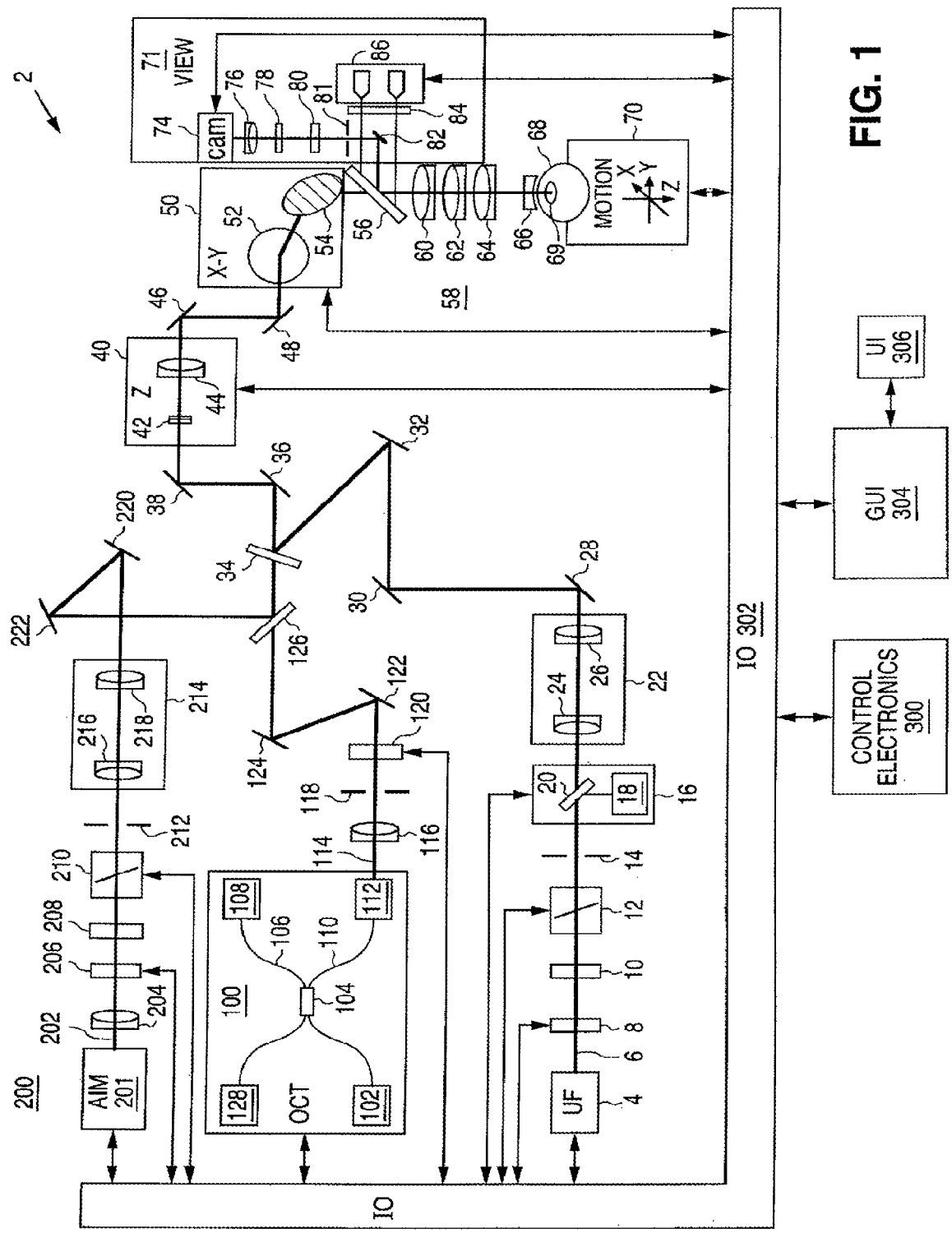
FIG. 1 is a schematic diagram of an ophthalmic laser system in which embodiments of the present invention may be implemented.

The present invention can be implemented by a system that projects or scans an optical beam into a patient's eye 68, such as system 2 shown in FIG. 1 which includes an ultrafast (UF) light source 4 (e.g. a femtosecond laser). Using this system, a beam may be scanned in a patient's eye in three dimensions: X, Y, Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser 4 may be a repetitively pulsed 1035 nm device that produces 500 fs pulses at a repetition rate of 100 kHz and an individual pulse energy in the ten microjoule range.

The laser 4 is controlled by control electronics 300, via an input and output device 302, to create optical beam 6. Control electronics 300 may be a computer, microcontroller, etc. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated UF light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the UF beam 6. Additionally, the orientation of linear polarizer 10 determines the incident polarization state incident upon beamcombiner 34, thereby optimizing beamcombiner throughput.

The UF beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light.

After exiting conditioning stage 22, beam 6 reflects off of fold mirrors 28, 30, & 32. These mirrors can be adjustable for alignment purposes. The beam 6 is then incident upon beam combiner 34. Beamcombiner 34 reflects the UF beam 6 (and transmits both the OCT 114 and aim 202 beams described below). For efficient beamcombiner operation, the angle of incidence is preferably kept below 45 degrees and the polarization where possible of the beams is fixed. For the UF beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40.

After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of UF focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An f-theta lens 58 of focal length 60 mm generating a spot size of 10 µm, over a field of 10 mm, with an input beam size of 15 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the optical beam 6 into the patient's eye 68 while helping to stabilize eye position. The positioning and character of optical beam 6 and/or the scan pattern the beam 6 forms on the eye 68 may be further controlled by use of an input device such as a joystick, or any other appropriate user input device (e.g. GUI 304) to position the patient and/or the optical system.

The UF laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 1, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information may then be loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs either time domain, frequency or single point detection techniques. In FIG. 1, a frequency domain technique is used with an OCT wavelength of 920 nm and bandwidth of 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the UF beam 6 in the focal plane and therefore the OCT beam 114 is smaller in diameter than the UF beam 6 at the beamcombiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beamcombiners 126 & 34. Mirrors 122 & 124 may be adjustable for alignment purposes and in particular for overlaying of OCT beam 114 to UF beam 6 subsequent to beamcombiner 34. Similarly, beamcombiner 126 is used to combine the OCT beam 114 with the aim beam 202 described below.

Once combined with the UF beam 6 subsequent to beamcombiner 34, OCT beam 114 follows the same path as UF beam 6 through the rest of the system. In this way, OCT beam 114 is indicative of the location of UF beam 6. OCT beam 114 passes through the z-scan 40 and x-y scan 50 devices then the objective lens 58, contact lens 66 and on into the eye 68. Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y Z of UF beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference atm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by a an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 6 in the focal plane and therefore aim beam 202 is of similar diameter to the UF beam at the beamcombiner 34 location. Because the aim beam is meant to stand-in for the UF beam 6 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beamcombiners 126 and 34, thereby fixing the polarization state and allowing for optimization of the beamcombiners' throughput. Of course, if a semiconductor laser is used as aim beam light source 200, the drive current can be varied to adjust the optical power.

The aim beam 202 proceeds through a shutter 210 and aperture 212. The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

The aim beam 202 next passes through a beam conditioning device 214. Beam parameters such as beam diameter, divergence, circularity, and astigmatism can be modified using one or more well known beaming conditioning optical elements. In the case of an aim beam 202 emerging from an optical fiber, the beam conditioning device 214 can simply include a beam expanding telescope with two optical elements 216 and 218 in order to achieve the intended beam size and collimation. The final factors used to determine the aim beam parameters such as degree of collimation are dictated by what is necessary to match the UF beam 6 and aim beam 202 at the location of the eye 68. Chromatic differences can be taken into account by appropriate adjustments of beam conditioning device 214. In addition, the optical system 214 is used to image aperture 212 to a desired location such as a conjugate location of aperture 14.

The aim beam 202 next reflects off of fold mirrors 222 & 220, which are preferably adjustable for alignment registration to UF beam 6 subsequent to beam combiner 34. The aim beam 202 is then incident upon beam combiner 126 where the aim beam 202 is combined with OCT beam 114. Beamcombiner 126 reflects the aim beam 202 and transmits the OCT beam 114, which allows for efficient operation of the beamcombining functions at both wavelength ranges. Alternatively, the transmit and reflect functions of beamcombiner 126 can be reversed and the configuration inverted. Subsequent to beamcombiner 126, aim beam 202 along with OCT beam 114 is combined with UF beam 6 by beamcombiner 34.

A device for imaging the target tissue on or within the eye 68 is shown schematically in FIG. 1 as imaging system 71. Imaging system includes a camera 74 and an illumination light source 86 for creating an image of the target tissue. The imaging system 71 gathers images which may be used by the system controller 300 for providing pattern centering about or within a predefined structure. The illumination light source 86 for the viewing is generally broadband and incoherent. For example, light source 86 can include multiple LEDs as shown. The wavelength of the viewing light source 86 is preferably in the range of 700 nm to 750 nm, but can be anything that is accommodated by the beamcombiner 56, which combines the viewing light with the beam path for UF beam 6 and aim beam 202 (beamcombiner 56 reflects the viewing wavelengths while transmitting the OCT and UF wavelengths). The beamcombiner 56 may partially transmit the aim wavelength so that the aim beam 202 can be visible to the viewing camera 74. Optional polarization element 84 in front of light source 86 can be a linear polarizer, a quarter wave plate, a half-wave plate or any combination, and is used to optimize signal. A false color image as generated by the near infrared wavelength is acceptable.

The illumination light from light source 86 is directed down towards the eye using the same objective lens 58 and contact lens 66 as the UF and aim beam 6, 202. The light reflected and scattered off of various structures in the eye 68 are collected by the same lenses 58 & 66 and directed back towards beamcombiner 56. There, the return light is directed back into the viewing path via beam combiner and mirror 82, and on to camera 74. Camera 74 can be, for example but not limited to, any silicon based detector array of the appropriately sized format. Video lens 76 forms an image onto the camera's detector array while optical elements 80 & 78 provide polarization control and wavelength filtering respectively. Aperture or iris 81 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 71.

Coarse adjust registration is usually needed so that when the contact lens 66 comes into contact with the cornea, the targeted structures are in the capture range of the X, Y scan of the system. Therefore a docking procedure is preferred, which preferably takes in account patient motion as the system approaches the contact condition (i.e. contact between the patient's eye 68 and the contact lens 66. The viewing system 71 is configured so that the depth of focus is large enough such that the patient's eye 68 and other salient features may be seen before the contact lens 66 makes contact with eye 68.

Preferably, a motion control system 70 is integrated into the overall control system 2, and may move the patient, the system 2 or elements thereof, or both, to achieve accurate and reliable contact between contact lens 66 and eye 68. Furthermore, a vacuum suction subsystem and flange may be incorporated into system 2, and used to stabilize eye 68. The alignment of eye 68 to system 2 via contact lens 66 may be accomplished while monitoring the output of imaging system 71, and performed manually or automatically by analyzing the images produced by imaging system 71 electronically by means of control electronics 300 via IO 302. Force and/or pressure sensor feedback may also be used to discern contact, as well as to initiate the vacuum subsystem.

Figure 2:
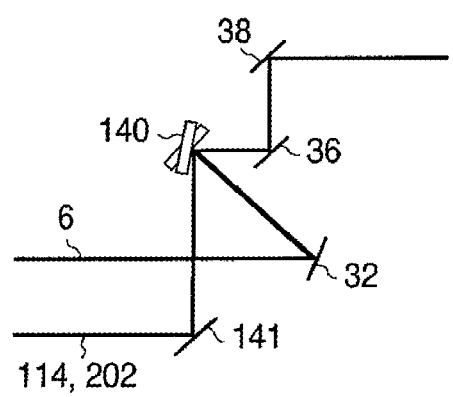
FIG. 2 is an optical diagram showing an alternative beam combining scheme for the ophthalmic laser system of FIG. 1.

An alternative beamcombining configuration is shown in the alternate embodiment of FIG. 2. For example, the passive beamcombiner 34 in FIG. 1 can be replaced with an active combiner 140 in FIG. 2. The active beamcombiner 34 can be a moving or dynamically controlled element such as a galvanometric scanning mirror, as shown. Active combiner 140 changes its angular orientation in order to direct either the UF beam 6 or the combined aim and OCT beams 202,114 towards the scanner 50 and eventually eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
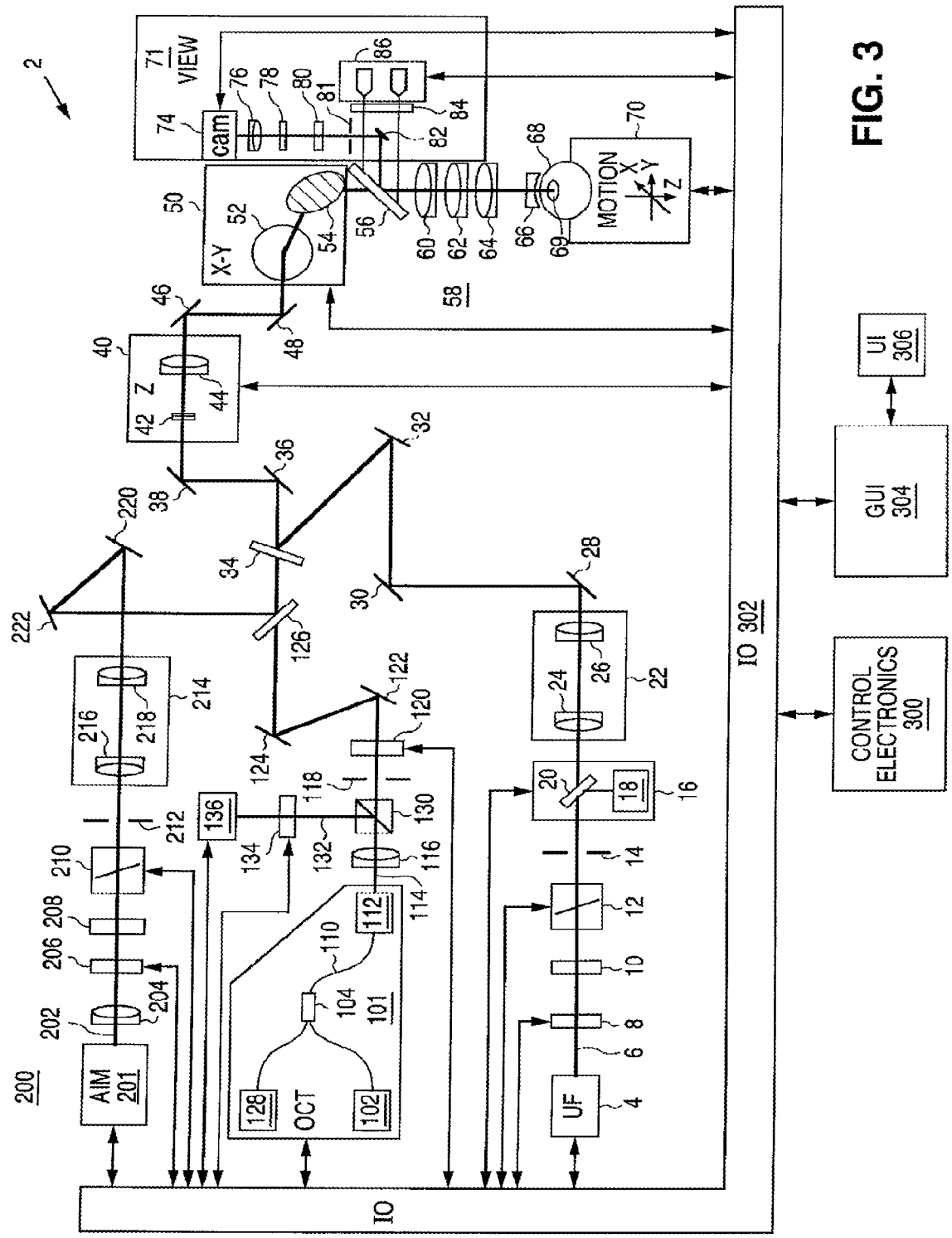
FIG. 3 is a schematic diagram of an ophthalmic laser system with an alternative OCT configuration in which embodiments of the present invention may be implemented.

Another alternate embodiment is shown in FIG. 3 which is similar to that of FIG. 1 but utilizes an alternate approach to OCT 100. In FIG. 3, OCT 101 is the same as OCT 100 in FIG. 1, except that the reference arm 106 has been replaced by reference arm 132. This free-space OCT reference arm 132 is realized by including beamsplitter 130 after lens 116. The reference beam 132 then proceeds through polarization controlling element 134 and then onto the reference return module 136. The reference return module 136 contains the appropriate dispersion and path length adjusting and compensating elements and generates an appropriate reference signal for interference with the sample signal. The sample arm of OCT 101 now originates subsequent to beamsplitter 130. The potential advantages of this free space configuration include separate polarization control and maintenance of the reference and sample arms. The fiber based beam splitter 104 of OCT 101 can also be replaced by a fiber based circulator. Alternately, both OCT detector 128 and beamsplitter 130 might be moved together as opposed to reference arm 136.

Figure 4:
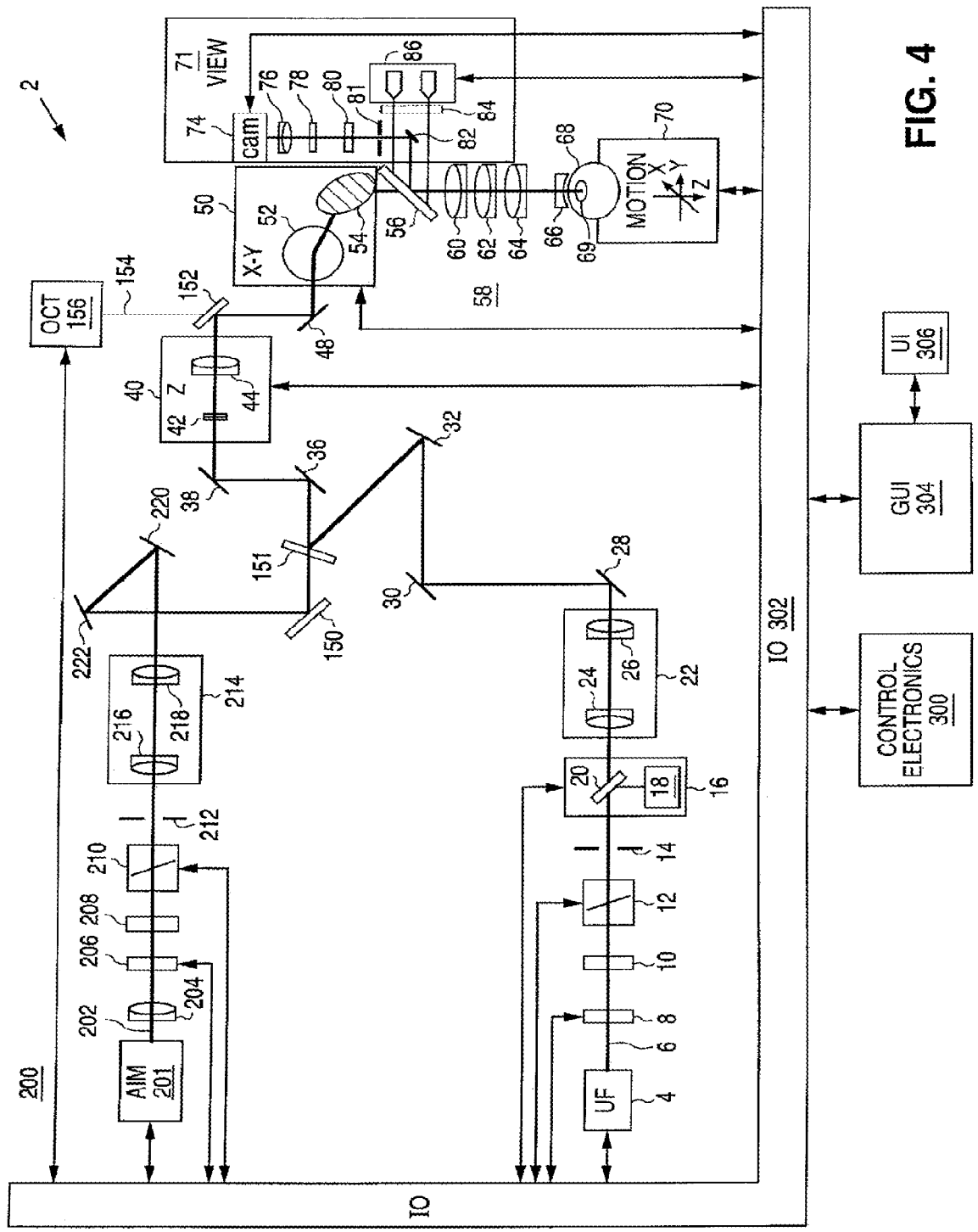
FIG. 4 is a schematic diagram of an ophthalmic laser system with another alternative OCT combining scheme in which embodiments of the present invention may be implemented.

FIG. 4 shows another alternative embodiment for combining OCT beam 114 and UF beam 6. In FIG. 4, OCT 156 (which can include either of the configurations of OCT 100 or 101) is configured such that its OCT beam 154 is coupled to UF beam 6 after the z-scan 40 using beamcombiner 152. In this way, OCT beam 154 avoids using the z-adjust. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc., as described in U.S. Pat. Nos. 5,748,898; 5,748,352; 5,459,570; 6,111,645; and 6,053,613 (which are incorporated herein by reference.)

In the above illustrated embodiments, the contact lens 66 can help to stabilize eye position. In other embodiments, the cornea is not in contact with a hard lens; rather, a fluid fills the space above the corneal anterior surface to act as an optical medium between the optical lens of the laser system and the cornea.

Other ophthalmic laser system structures may be employed, such as that described in U.S. Pat. Appl. Pub. No. 2015/0141972, the disclosure of which is incorporated herein by reference.

As mentioned earlier, precise laser delivery during treatment is paramount in laser eye surgery in general, and in particular, for example, when forming arcuate incisions in the cornea in cataract surgery. Embodiments of the present invention provide a method of operating the ophthalmic laser system that can improve the precision of laser delivery during treatment and address the problem of patient movement.

The operating method according to embodiments of the present invention can be implemented in the above-described ophthalmic laser systems to achieve real-time OCT imaging while laser treatment is being conducted. More specifically, embodiments of the present invention provide a method of controlling and operating the ophthalmic laser system, where the UF laser 4, the OCT device 100, and the optical scanning system are operated to simultaneously deliver the focus of the UF light (treatment light) beam 6 and the focus of the OCT beam 114 to the same location in the patient's eye, and to obtain real-time OCT measurement data while the treatment laser treats the eye.

The OCT technique constructs images by aggregating A-scans. An A-scan is a vertical one-dimensional (1D) array of intensity values, each value representing the intensity of returned sample light that has been reflected and scattered by the sample at a particular depth. In time domain OCT, an A-scan is formed one depth value at a time; the reference pathlength is changed by scanning the mirror of the reference arm to obtain data for different depths. In frequency domain OCT, which employs a broad band (e.g. 100 nm bandwidth) light source and spectrally separated detectors, an entire A-scan is calculated at once from the acquired spectral data, without scanning the reference pathlength.

In conventional OCT techniques, each A-scan is produced while the OCT sample beam is directed to a point of the sample and remains stationary. A two-dimensional (2D) or three-dimensional (3D) image can be constructed by sequentially producing adjacent A-scans at different lateral (X-Y) positions, then aggregating them into the 2D or 3D image.

In embodiments of the present invention, the treatment laser focus and the OCT beam focus are delivered simultaneously, by the optical system of the ophthalmic laser system, into the patient's eye. The treatment laser focus and the OCT beam focus coincide with each other in space, and both are scanned simultaneously by the same X-Y scanner in the horizontal directions. The scan pattern is determined based on treatment need. During a time interval when the OCT beam focus is scanned in a horizontal line (straight or curved) within the eye tissue, the returned OCT light is recorded by the OCT detector, and used to produce an A-scan using frequency domain OCT technology. Even though the OCT beam is being scanning in the eye tissue, the returned OCT light is recorded and processed in the normal manner by the OCT system, i.e., as if the OCT beam were stationary in the eye tissue. In other words, from the standpoint of the OCT detector and data processing algorithm, no change is required as to how an A-scan is generated. In effect, the returned OCT light during that time interval is averaged to obtain the A-scan.

As schematically illustrated in FIG. 5, the portion of the sample that contributes to the signal for the A-scan is a two dimensional section 501 (referred to as the OCT sampling section in this disclosure) which extends in the depth (Z) direction, where the projection of the sampling section onto the horizontal X-Y plane is along the scan line 502 of the OCT beam (and the treatment laser beam). The scan line may be straight or curved. Each data point (pixel) 503 of the A-scan, schematically represented by the dots in FIG. 5, can be considered as resulting from the average intensity of the returned OCT light from the same depth, i.e., along a horizontal line segment 504 in the sampling section parallel to the scan line, as schematically represented by the dashed lines in FIG. 5. These horizontal line segment are referred to as horizontal OCT sampling lines in this disclosure.

Thus, although the laser treatment scan moves the OCT light focus faster than that required for the OCT light to remain stationary during a full A-scan data acquisition cycle, the OCT system will construct an A-scan using the average intensity of the returned light from the OCT sampling section corresponding to the data acquisition period.

In some embodiments, the data acquisition period T, i.e. the amount of time required by the OCT system to generate an A-scan, is approximately 1 ms, while the scanning speed of the X-Y scanner is approximately 100-600 mm/s. Thus, taking a scanning speed of 600 mm/s as an example, the length L of the scan line segment that the OCT beam traverses during the data acquisition period T is approximately 0.6 mm. The treatment scan pattern should be designed such that the time it takes to scan one continuous line in the treatment pattern is longer than the OCT data acquisition period. If the continuous scan lines in the treatment scan pattern are short, the scan speed can be reduced to meet the above requirement.

When the eye tissue structure is such that the reflection and scattering properties at points along each horizontal OCT sampling line are relatively constant, but the properties at different depths vary, then the A-scan obtained while scanning the OCT beam horizontally will represent the vertical variation of the sample structure in the OCT sampling section. This is the case, for example, when performing a scan to form an arcuate incision in the cornea during cataract surgery, described in further detail below.

The shape of an arcuate incisions is a part of a conical surface that crosses both the anterior and posterior surfaces of the cornea. As shown in FIGS. 6A and 6B, the arcuate incision is an arc shape in the en face view (i.e. in a cross-section perpendicular to the axis of the eye), and an approximately straight line in a vertical cross-sectional view (i.e. in a cross-section that passes through the axis of the eye). The arcuate incision is formed by scanning the treatment laser focus in a vertical raster pattern, scanning horizontal arcs back and forth, each arc slightly higher or lower than the previous. These arcs lay on the surface of a cone that transverses the cornea. During the scan for each arc, the distances of the arc to both the anterior and posterior corneal surfaces are approximately constant as the laser focus moves along the horizontal arc. Thus, during such a scan, the tissue structures along each horizontal OCT sampling line have similar reflection and scattering properties and therefore produce relatively constant returned OCT light from that depth. For a horizontal OCT sampling line that is at or near the corneal surface (see FIG. 5, which schematically indicates an intersection line 505 of the anterior corneal surface with the OCT sampling section), the A-scan pixel corresponding to that depth will represent the reflection and scattering properties of the corneal surface and its vicinity. For a horizontal OCT sampling line located entirely above the corneal surface and inside the optical medium (contact lens or liquid), the A-scan pixel corresponding to that depth will represent the reflection and scattering properties of the optical medium. This way, the A-scan can be used to detect corneal surface and calculate the depth-direction distance between the corneal surface and the focus position of the OCT beam (and hence the treatment laser focus, which coincides with the OCT beam focus). This knowledge may then be used to confirm or adjust the laser treatment scan pattern, such as to confirm or adjust when the incision is completed and the scanning should stop.

In some embodiments, the frequency domain OCT produces A-scans of 512 pixels representing a depth range of about 4 to 5 mm in water, giving it a depth resolution of approximately 8-10 μm per pixel. Thus, when forming an arcuate incision, the A-scans can show the corneal surface location with sufficient precision for the purpose of maintaining a minimum uncut distance of approximately 100 μm from the posterior corneal surface.

As mentioned earlier, in some embodiments, when the scan speed is approximately 600 mm/s and the OCT data acquisition time is approximately 1 ms, the length L of the scan line that the OCT beam traverses during a data acquisition period T is approximately 0.6 mm. Thus, if each horizontal arc of the arcuate incision scan pattern is substantially longer than 0.6 mm, multiple A-scans can be obtained for each horizontal arc (see FIG. 6C). For example, if the arc is approximately 2 mm long, three A-scans can be produced along the arc. In such a situation, the multiple A-scans along the same arc can also be used detect any tilt of the corneal surface relative to the arc (i.e. relative to the horizontal direction of the laser system). This is because when the corneal surface is tilted, the corneal surface location detected in the A-scans will change from one A-scan to another. Such changes can be used to calculate the tilt of the corneal surface.

The A-scans obtained simultaneously with the laser treatment scan can also be used to detect patient movement in real time. For example, patient movement in the Z direction will cause the corneal surface location in the A-scans to change from one A-scan to another. Note that the effect of corneal surface tilt and patient movement on the A-scans can be distinguished from each other based on the fact that the corneal surface tilt produces a more systematic change in the detected corneal surface location while patient movement produces a more random change. In response to detected patient movement, the depth of the treatment laser focus (and the OCT sample beam focus) may be adjusted, or treatment may be halted.

While the above descriptions use an arcuate corneal incision as an example, the real-time OCT monitoring method according to embodiments of the present invention is also useful in other ophthalmic applications where the eye tissue structure is relatively similar in the horizontal direction (parallel to the horizontal scan line) but varies in the depth direction. Examples of such applications include cutting a primary incision or sideport incision in the cornea in a cataract procedure; cutting a capsulotomy when the cut is centered on the axis of the lens capsule, where the circular scan lines are at approximately the same depth from the surface of the lens capsule; etc.

In the capsulotomy application, if the lens capsule is tilted relative to the optical axis of the eye but the circular capsulotomy scan lines are centered on the optical axis, the depth-direction distance between the circular scan line and the lens capsule surface will vary over the circular scan. This may adversely impact the quality of the A-scans, and the lens capsule surface may not be clearly defined in the A-scans. In an example illustrated in FIG. 5, the lens capsule is tilted such that the intersection line 506 (the dash-dotted line in FIG. 5) of the lens capsule surface and an OCT sampling section is not parallel to the horizontal direction, then some horizontal OCT sampling lines near the lens capsule surface may cross the lens capsule surface during the OCT data acquisition period. As a result, the average intensity of the returned OCT light from this depth will be impacted. Note that in FIG. 5, both the tilted surface and the spacing of the A-scan pixels are exaggerated. If, at the location of the OCT sampling section, the lens capsule surface is tilted by 1 degree from the horizontal direction, and the length L of the OCT sampling section is 0.6 mm, then the depth of the lens capsule surface will change by approximately 10 μm within the length L. This value is similar to the depth resolution of the A-scan (8-9 μm). The depth variation within an acquisition period can be reduced by reducing the horizontal scan speed of the treatment light and OCT sample beam.

In embodiments of the present invention, the treatment laser and the OCT light have different wavelength ranges. Therefore, even though the treatment laser beam and the OCT beam are simultaneously delivered to the eye tissue, the reflected or scattered treatment laser light can be prevented from entering the OCT detector, e.g., by a color filter in the OCT system, to avoid noise caused by the treatment laser. In one embodiment, the treatment laser has a wavelength of approximately 1030 nm, and the OCT light has a wavelength of approximately 920 nm and a bandwidth of approximately 100 nm.

FIG. 7 summarizes the operation of the ophthalmic laser system according to embodiments of the present invention. First, the ultrafast laser source and the OCT device are used to simultaneously generate a treatment laser beam and an OCT beam, respectively (step S701). The focus of the treatment laser beam and the focus of the OCT beam are simultaneously delivered to a sample (an eye tissue) using the optical delivery system (step S702). The focus of the treatment laser beam and the focus of the OCT beam coincide with each other in space. This step includes simultaneously scanning, using the same scanning device, the focuses of the treatment laser beam and OCT beam in a horizontal direction according to a treatment scan pattern. While the OCT beam is being scanned in the sample, the OCT device detects returned OCT light from the sample during a data acquisition period, and generates an A-scan using the detected light (step S703). The technique used to generate the A-scan is the same as in conventional OCT technologies such as frequency domain OCT. The A-scan represents variations of the sample structure in the depth direction. A controller of the ophthalmic laser system (e.g. the control electronics 300) analyzes the A-scan to determine a structure of the sample in the depth direction relative to the focus of the OCT beam (step S704). For example, the controller can determine the depth-direction distance between a corneal surface and the focus of the OCT beam. Based on such determinations, the controller controls the operation of the ophthalmic laser system, including the operations of the ultrafast laser, the OCT device, and the scanners (step S705). This control may include adjusting the position of the scan pattern, determining when scanning should stop, etc. In all of the above steps, the operations of the ultrafast laser, the OCT device and the optical delivery system may be controlled by the controller of the ophthalmic laser system.

To summarize, the real-time OCT measurement method according to embodiments of the present invention can monitor the eye tissue structure with the OCT signal while treating the eye. The process measures the OCT signal, while the OCT beam focus is moved in the eye by the X-Y scanner, while treatment is happening.

In one aspect, the present invention provides a process of operating an ophthalmic laser system. In another aspect, the present invention provides an ophthalmic laser system having, inter alia, a controller that is configured to control the ophthalmic laser system to perform the process. In another aspect, the present invention provides a computer program product comprising a computer usable non-transitory medium (e.g. memory or storage device) having a computer readable program code embedded therein, the computer readable program code being configured to cause the ophthalmic laser system to perform the process.

It will be apparent to those skilled in the art that various modification and variations can be made in the ophthalmic laser system and related method of the present invention without departing from the spirit or scope of the invention. Thus, it is intended that the present invention cover modifications and variations that come within the scope of the appended claims and their equivalents.

What is claimed is:

1. An ophthalmic laser surgical method, comprising:
   a laser device and an optical coherence tomography (OCT) device simultaneously generating a treatment laser beam and an OCT light beam, respectively;
   an optical delivery system simultaneously delivering a focus of the treatment laser beam and a focus of the OCT light beam to a sample, the sample including a patient's eye, wherein the focus of the treatment laser beam and the focus of the OCT light beam coincide with each other in space, and simultaneously scanning the focus of the treatment laser beam and the focus of the OCT light beam, during a data acquisition period, in a horizontal line in the sample which is perpendicular to a depth direction;

the OCT device detecting returned OCT light from the sample during the data acquisition period while the focus of the treatment laser beam and the focus of the OCT light beam are simultaneously scanned in the sample in the horizontal line, and generating an OCT A-scan based on the detected OCT light returned from the sample during the entire data acquisition period, the A-scan being a one-dimensional array of intensity values in the depth direction representing structural properties of the sample; and a controller analyzing the A-scan to determine a structure of the sample in the depth direction relative to the focus of the OCT light beam, and based on the determination, controlling operations of the laser source, the OCT device and the optical delivery system.

2. The method of claim 1, wherein the OCT device is a frequency domain OCT device.

3. The method of claim 1, wherein the step of simultaneously scanning includes using an X-Y scanner to simultaneously scan the focus of the treatment laser beam and the focus of the OCT light in a horizontal direction which is perpendicular to the depth direction.

4. The method of claim 3, wherein the scanning is performed according to a treatment scan pattern.

5. The method of claim 4, wherein the treatment scan pattern defines an arcuate incision in a cornea of the patient's eye.

6. The method of claim 5, wherein the step of analyzing the A-scan includes determining a depth-direction distance between a corneal surface and the focus of the OCT light.

7. The method of claim 3, wherein the focus of the treatment laser beam and the focus of the OCT light are simultaneously scanned along a continuous scan line in the horizontal direction, and wherein the OCT device detects returned OCT light from the sample during multiple data acquisition periods while the focus of the OCT light is being scanned in respective multiple different portions of the continuous scan line to generate multiple A-scans.

8. The method of claim 7, wherein the step of analyzing the A-scan includes determining a tilt of a tissue structure relative to the horizontal direction by comparing the multiple A-scans.

9. The method of claim 7, wherein the step of analyzing the A-scan includes determining a movement of the patient's eye in the vertical direction by comparing the multiple A-scans.

10. The method of claim 3, wherein a length of the horizontal line of the sample that the OCT light beam is scanned in during the data acquisition period is 0.1-0.6 mm.

11. An ophthalmic surgical laser system, comprising:
a laser device configured to generate a treatment laser beam;
an optical coherence tomography (OCT) device configured to generate an OCT light beam, and to detect a returned OCT light from a sample during a data acquisition period to generate an OCT A-scan based on the detected OCT light, the A-scan being a one-dimensional array of intensity values in a depth direction representing structural properties of the sample;
an optical delivery system configured to deliver a focus of the treatment laser beam and a focus of the OCT light beam to the sample, the sample including a patient's eye; and
a controller coupled to the laser device, the OCT device and the optical delivery system, configured to:
control the laser device and the OCT device to simultaneously generate the treatment laser beam and the OCT light beam, respectively;
control the optical delivery system to simultaneously deliver the focus of the treatment laser beam and the focus of the OCT light beam to the sample and simultaneously scan the focus of the treatment laser beam and the focus of the OCT light beam, during a data acquisition period, in a horizontal line in the sample which is perpendicular to the depth direction, wherein the focus of the treatment laser beam and the focus of the OCT light beam coincide with each other in space;
control the OCT device to generate an A-scan during the data acquisition period while the focus of the treatment laser beam and the focus of the OCT light beam are simultaneously scanned in the horizontal line in the sample, wherein the A-scan is generated based on detected OCT light returned from the sample during the entire data acquisition period, and analyze the A-scan to determine a structure of the sample in the depth direction relative to the focus of the OCT light beam; and
based on the determination, control operations of the laser source, the OCT device and the optical delivery system.

12. The laser system of claim 11, wherein the OCT device is a frequency domain OCT device.

13. The laser system of claim 11, wherein the optical delivery system includes an X-Y scanner, and wherein the controller is configured to control the X-Y scanner to simultaneously scan the focus of the treatment laser beam and the focus of the OCT light in a horizontal direction which is perpendicular to the depth direction.

14. The laser system of claim 13, wherein the controller controls the X-Y scanner according to a treatment scan pattern.

15. The laser system of claim 14, wherein the treatment scan pattern defines an arcuate incision in a cornea of the patient's eye.

16. The laser system of claim 15, wherein the controller is configured to determine, based on the A-scan, a depth-direction distance between a corneal surface and the focus of the OCT light.

17. The laser system of claim 13, wherein the controller is configured to control the X-Y scanner to simultaneously scan the focus of the treatment laser beam and the focus of the OCT light are along a continuous scan line in the horizontal direction, receive multiple A-scans generated by the OCT device during multiple data acquisition periods while the focus of the OCT light is being scanned in respective multiple different portions of the continuous scan line.

18. The laser system of claim 17, wherein the controller is configured to determine a tilt of a tissue structure relative to the horizontal direction by comparing the multiple A-scans.

19. The laser system of claim 17, wherein the controller is configured to determine a movement of the patient's eye in the vertical direction by comparing the multiple A-scans.

20. The laser system of claim 13, wherein a length of the horizontal line of the sample that the OCT light beam is scanned in during the data acquisition period is 0.1-0.6 mm.

* * * * *